United States Patent [19]

Zilch et al.

[11] Patent Number: 5,543,561
[45] Date of Patent: Aug. 6, 1996

[54] ACYCLIC AMIDINE GROUP-CONTAINING DIPHOSPHONIC ACID DERIVATIVES, PROCESSES FOR THEIR PREPARATION AND MEDICAMENTS CONTAINING THESE COMPOUNDS

[75] Inventors: Harald Zilch, Mannheim; Frieder Bauss, Neuhofen, both of Germany

[73] Assignee: Boehringer Mannheim GmbH, Mannheim, Germany

[21] Appl. No.: 367,325

[22] PCT Filed: Jul. 13, 1993

[86] PCT No.: PCT/EP93/01833

§ 371 Date: Mar. 28, 1995

§ 102(e) Date: Mar. 28, 1995

[87] PCT Pub. No.: WO94/02492

PCT Pub. Date: Feb. 3, 1994

[30] Foreign Application Priority Data

Jul. 21, 1992 [DE] Germany ............ 42 23 940.0

[51] Int. Cl.$^6$ ................ C07F 9/38; A61K 31/66
[52] U.S. Cl. .............. 562/13; 514/107; 514/108; 558/158
[58] Field of Search .............. 562/13; 514/107, 514/108; 558/158

[56] References Cited

U.S. PATENT DOCUMENTS

| | | | |
|---|---|---|---|
| 4,705,651 | 11/1987 | Staibano | 260/502.5 C |
| 5,281,748 | 1/1994 | Jaeggi | 562/13 |
| 5,294,608 | 3/1994 | Lang et al. | 514/108 |
| 5,366,965 | 11/1994 | Strein | 514/102 |
| 5,366,969 | 11/1994 | Bosies et al. | 514/81 |
| 5,395,826 | 3/1995 | Naumann et al. | 514/107 |

FOREIGN PATENT DOCUMENTS

0576396A1  6/1993  European Pat. Off.

*Primary Examiner*—C. Warren Ivy
*Assistant Examiner*—Barbara S. Frazier
*Attorney, Agent, or Firm*—Nikaido, Marmelstein, Murray & Oram LLP

[57] ABSTRACT

Compounds of the formula I

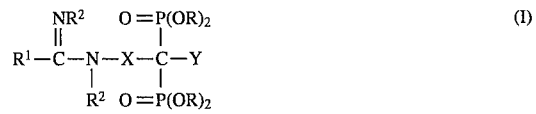

in which $R^1$ signifies hydrogen, a straight-chained, branched, saturated or unsaturated alkyl radical with 1–9 carbon atoms possibly substituted by phenyl or a phenyl ring which is possibly substituted by $C_1$–$C_3$alkyl, $C_1$–$C_3$-alkoxy or halogen, $R^2$ signifies hydrogen or $C_1$–$C_3$-alkyl, whereby the two radicals can be the same or different, R represents hydrogen or a straight-chained or branched alkyl radical with 1–4 carbon atoms, X signifies an alkylene chain with 1–6 carbon atoms which can be substituted one or more times by $C_1$–$C_3$-alkyl and can possibly be interrupted by oxygen, whereby 1 or 2 carbon stems of the alkylene chain can possibly be part of a cyclopentyl or cyclohexyl ring and Y signifies hydrogen, hydroxyl or amino group possibly substituted by alkyl groups with 1–6 carbon atoms, as well as their pharmacologically acceptable salts, processes for their preparation, as well as medicaments for the treatment of calcium metabolism disturbances.

12 Claims, No Drawings

ACYCLIC AMIDINE GROUP-CONTAINING DIPHOSPHONIC ACID DERIVATIVES, PROCESSES FOR THEIR PREPARATION AND MEDICAMENTS CONTAINING THESE COMPOUNDS

The present invention concerns new amidine group-containing diphosphonic acid derivatives, processes for their preparation, as well as medicaments which contain these substances.

In DE 18 13 659 are described diphosphonic acid derivatives of which 1-hydroxyethane-1,1-diphosphonic acid has achieved importance as agent for the treatment of Paget's disease.

EP-A-282,320 describes substituted 3-isoxazolyl-aminomethylenediphosphonic acids and their esters with antihypercalcaemic and antiarthritic action.

In EP-A-282,309 there are described "azol"-aminomethylenediphosphonic acids as hypercalcaemic inhibitors.

Furthermore, from JP-A-63/150 290 one knows aminomethylenediphosphonic acids as regulators of the calcium metabolism and from EP-A-274,158 tetrahydropyrimidinyl- and tetrahydropyridylaminomethylenediphosphonic acids for the treatment of an abnormal calcium and phosphate metabolism.

One knows cyclic amidine group-containing geminal diphosphonic acids from DE-A-3 208 600, Liebigs Ann. Chem. 1982, 275 and DE-A-39 30 130.3.

It has now been found that acyclic derivatives of these compounds are extraordinarily good calcium complex formers but, in addition, also show an excellent action on the calcium metabolism and thus are suitable for the broad treatment of calcium metabolism disturbances. Above all, they can be very well used there where the bone build-up and breakdown is disturbed, i.e. they are suitable for the treatment of diseases of the skeletal system, such as e.g. osteoporosis, Paget's disease, Bechterew's disease and the like.

However, on the basis of these properties, they also find use in the therapy of bone metastases, of urolithiasis and for the prevention of heterotopic ossifications. Furthermore, by means of their influencing of the calcium metabolism, they form a basis for the treatment of rheumatoid arthritis, of osteoarthritis and of degenerative arthrosis.

Consequently, the subject of the present invention are diphosphonates of the general formula I

in which $R^1$ signifies hydrogen, a straight-chained, branched, saturated or unsaturated alkyl radical with 1–9 carbon atoms possibly substituted by phenyl or a phenyl ring which is possibly substituted by $C_1$–$C_3$-alkyl, $C_1$–$C_3$-alkoxy or halogen, $R^2$ signifies hydrogen or $C_1$–$C_3$-alkyl, whereby the two radicals can be the same or different, R represents hydrogen or a straight-chained or branched alkyl radical with 1–4 carbon atoms, X signifies an alkylene chain with 1–6 carbon atoms which can be substituted one or more times by $C_1$–$C_3$-alkyl and can possibly be interrupted by oxygen, whereby 1 or 2 carbon atoms of the alkylene chain can possibly be part of a cyclopentyl or cyclohexyl ring and Y signifies hydrogen, hydroxyl or amino possibly substituted by alkyl groups with 1–6 carbon atoms, as well as their pharmacologically acceptable salts.

Y preferably stands for hydrogen, hydroxyl or amino group which can be substituted by methyl, ethyl or isopropyl.

For the group X, there preferably comes into question an ethylene, propylene, butylene, 1-methylpropylene, 2-methylpropylene, 1-methylbutylene or 2-methylbutylene radical.

Furthermore, X preferably represents a 1,1- or 1,2-substituted cyclohexyl or cyclopentyl ring which is connected to the biphosphonic acid part via methylene, ethylene or propylene.

R preferably signifies hydrogen or the methyl, ethyl or isobutyl radical.

Compounds are especially preferred in which R and $R^2$ is hydrogen, Y signifies hydrogen or hydroxyl group and $R^1$ represents hydrogen or an alkyl radical.

X stands especially preferably for methylene, ethylene, propylene or butylene radical.

The compounds can be present as stereoisomeric mixture or as pure cis or trans isomers.

Asymmetric carbon atoms can possess the R- or S-configuration and the compounds can be present optically-active or as racemates.

The compounds of gen. formula I are prepared according to per se known processes, preferably in that one reacts a carboxylic acid of the general formula II

in which $R^1$ $R^2$ and X have the above-given meaning, with a mixture of phosphorous acid or phosphoric acid and a phosphorus halide or phosphoryl halide or can bring the phosphorus halide to reaction alone in the presence of water and subsequently hydrolyses to the free diphosphonic acid or, if desired, converts the isolated compounds of the general formula I into their esters or into pharmacologically acceptable salts.

The carboxylic acids of the formula II are new and can be prepared in that one a) reacts acrylic esters with amidines of the general formula III

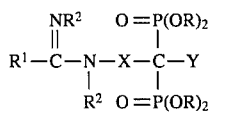

and hydrolyses the esters to the corresponding free carboxylic acids, b) opens pyrimidinones of the general formula IV

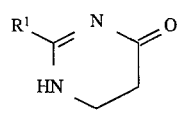

with alkali metal or alkaline earth metal hydroxides and converts into the free acid, c) brings nitriles of the formula V

to reaction with amines and saponifies the ester group $R^E$, or d) reacts an activated compound of the formula VI

in which Z represents e.g. a halogen atom, with an amidine of the formula III and obtains the free acid after ester hydrolysis.

The carboxylic acids of gen. formula II used in the preparation processes are mixed with 1–5, preferably 2–3 mol of phosphorous acid or phosphoric acid and 1–5, preferably 2–3 mol of phosphoryl halide, phosphorus trihalide or phosphorus pentahalide and brought to reaction at 80°–130° C. preferably 100° C. In the case of the phosphorus or phosphoryl halides, it is preferably a question of the chlorides or bromides. One can also carry out the reaction in the presence of diluents, such as halogenated hydrocarbons, especially chlorobenzene, tetrachloroethane, but also dioxane, possibly with the addition of water. The subsequent hydrolysis takes place by heating with water but expediently with semi-concentrated hydrochloric or hydrobromic acid.

The free diphosphonic acids of the general formula I can be converted into the corresponding tetraalkyl esters by heating with orthoformic acid alkyl esters and saponified to diesters or again to the free tetraacids. As a rule, the saponification to diesters takes place in that one treats the tetraalkyl esters with an alkali metal halide, preferably sodium iodide, in a suitable solvent, such as e.g. acetone, at room temperature.

There hereby results the symmetrical diester/disodium salt which can possibly be converted by means of an acidic ion exchanger into the diester/diacid. The saponification of the esters to free diphosphonic acids takes place, as a rule, by boiling with hydrochloric or hydrobromic acid. However, one can also carry out a cleavage with a trimethylsilyl halide, preferably the bromide or iodide.

As pharmacologically acceptable salts, there are, above all, used mono- or dialkali metal or ammonium salts, which are prepared in the usual way, e.g. by titration of the compounds with inorganic or organic bases, such as e.g. sodium or potassium hydrogen carbonate, caustic soda solution, caustic potash solution, aqueous ammonia or amines, such as trimethyl-, triethyl- or cyclohexylamine. Furthermore, calcium, zinc and magnesium salts are of especial importance.

As a rule, the salts are purified by reprecipitation from water/methanol or water/acetone.

The new substances of the formula I according to the invention and their salts can be administered enterally or parenterally in liquid or solid form. There hereby come into question all usual forms administration, for example tablets, capsules, dragees, syrups, solutions, suspensions etc. As injection medium, water is preferably used which contains the additives usual in the case of injection solutions, such as stabilising agents, solubilising agents and buffers.

Such additives are e.g. tartrate and citrate buffers, ethanol, complex formers (such as ethylene-diamine-tetraacetic acid and its non-toxic salts), high molecular polymers (such as liquid polyethylene oxide) for viscosity regulation. Liquid carrier materials for injection solutions must be sterile and are preferably filled into ampoules. Solid carrier materials are e.g. starch, lactose, mannitol, methyl. cellulose, talc, highly dispersed silicic acids, high molecular fatty acids (such as stearic acid), gelatine, agar-agar, calcium phosphate, magnesium stearate, animal end vegetable fats, solid high molecular polymers (such as polyethylene glycols); compositions suitable for oral administration can, if desired, contain flavouring and sweetening agents.

The dosaging can depend upon various factors, such as mode of administration, species, age and/or individual state of health. The daily dosage to be administered lies at about 1–1000 mg/human, preferably 10–200 mg/human and can be taken all at once or divided up several times.

Preferred in the meaning of the present invention are, apart from the compounds mentioned in the Examples and compounds derivable by combination of all meanings of the substituents mentioned in the claims, the following diphosphonic acids, as well as their sodium salts, methyl and ethyl esters:

Preferred compounds:
1) 1-hydroxy-2-(1-iminoethyl)-aminoethane-1,1-diphosphonic acid
2) 1-hydroxy-4-(1-iminoethyl)-aminobutane-1,1-diphosphonic acid
3) 1-hydroxy-5-(1-iminoethyl)-aminopentane-1,1-diphosphonic acid
4) 1-hydroxy-3-(1-iminopropyl)-aminopropene-1,1-diphosphonic acid
5) 1-hydroxy-4-(1-iminobutyl)-aminobutene-1,1-diphosphonic acid
6) 1-hydroxy-6-(1-iminoethyl)-aminohexane-1,1-diphosphonic acid
7) 1-hydroxy-3-(1-iminoethyl)-aminobutane-1,1-diphosphonic acid
8) 1-hydroxy-4-(iminoethyl)-aminopentane-1,1-diphosphonic acid
9) 1-hydroxy-5-(1-iminoethyl)-aminohexane-1,1-diphosphonic acid
10) 1-hydroxy-3-(1-iminopropyl)-aminobutane-1,1-diphosphonic acid
11) 1-hydroxy-4-(iminoethyl)-amino-3-methylbutane1,1-diphosphonic acid
12) 1-hydroxy-3-(1-iminobutyl)-aminopropane-1,1-diphosphonic acid
13) 1-hydroxy-3-[1-(methylimino)-ethyl]-aminopropane-1,1-diphosphonic acid
14) 1-hydroxy-3-[2-(1-iminoethyl)-aminocyclohexyl]-propane-1,1-diphosphonic acid
15) 1-hydroxy-3-[2-(1-iminoethyl)-aminocyclopentyl]-propane-1,1-diphosphonic acid
16) 1-hydroxy-3-[1-(1-iminoethyl)-aminocyclohexyl]-propane-1,1-diphosphonic acid
17) 1-hydroxy-2-[2-(1-iminopropyl)-aminocyclohexyl]-ethane-1,1-diphosphonic acid
18) 1-hydroxy-2-(iminomethyl)-aminoethane-1,1-diphosphonic acid
19) 3-(iminoethyl)-aminoethane-1,1-diphosphonic acid
20) 2-(1-iminoethyl)-aminoethane-1,1-diphosphonic acid
21) 1-hydroxy-3-(iminomethyl)-aminopropane-1,1-diphosphonic acid
22) 3-(1-iminoethyl)-aminopropane-1,1-diphosphonic acid
23) 3-[2-(1-iminoethyl)-aminocyclohexyl]-propane-1,1-diphosphonic acid
24) 1-hydroxy-3-[2-(iminomethyl)-aminocyclohexyl]-propane-1,1-diphosphonic acid

EXAMPLE 1

2-Methyl-5,6-dihydro-1H-pyrimidin-4-one 14 g acetamidine hydrochloride were introduced into a solution of 3.4 g sodium in 118 ml abs. ethanol and stirred for 30 minutes at room temperature.

Then, within 30 minutes, 15.4 ml acrylic acid methyl ester were added dropwise thereto and stirred for a further 5 hours at room temperature.

After addition of 100 ml acetone, the precipitate was filtered off with suction, the filtrate evaporated in a vacuum and the residue recrystallised from ethanol. Yield 13.5 g (56% of theory ); m.p. 127°–131° C. (according to NMR in DMSO, it is a question of the enol form ).

3-(1-Iminoethyl)-aminopropionic acid 4 g 2-Methyl-5,6-dihydro-1H-pyrimidin-4-one were heated for 5 hours at 50° C. in 350 ml of water with 20 g Ba(OH)$_2$33 8H$_2$O.

One then allowed to cool to room temperature, filtered off the white precipitate present and acidified the filtrate with 2N H$_2$SO$_4$.

After standing for 20 hours in a refrigerator, the precipitated BaSO$_4$ was filtered off with suction, the filtrate evaporated in a rotary evaporator and the residue precipitated from ethanol with ether. Without further purification, the dried precipitate was used for the phosphorylation.

1-Hydroxy-3-(iminoethyl)-aminopropane-1,1-diphosphonic acid 5 g 3-(1-Iminoethyl)-aminopropionic acid were melted with 6.7 g H$_3$PO$_3$ at 80° C. slowly mixed with 7.5 ml POCl$_3$ while stirring slowly and maintained 80° C. for 24 hours.

The excess POCl3 was then stripped off in a vacuum, the residue mixed with 80 ml of water and the clear solution heated to 100° C. for 1 hour.

After cooling, it was evaporated in a rotary evaporator and purified by ion exchanger chromatography on Amberlite IR 120 (H$^+$ form), with water as eluent.

The fraction uniform according to TLC were combined, evaporated and crystallised from water/acetone. Yield 5.2 g (53% of theory, referred to the 2-methyl-5,6-dihydro-1H-pyrimidin-4-one used); m.p. >106° C. (decomp.); $R_f$=0.36 (EtOH/H$_2$O/HOAc 9/1/1/).

Retinoid test

The carrying out of the experiment took place with reference to the method of Trechsel, Stutzer and Fleisch (J. Clin. Invest., 80, 1679–1686, 1987) in thyreoparathyroidectomised rats (TPTX). For reasons of comparability with the literature and with previously obtained external data, the dosage statements for the biphosphonates take place in mg P/kg (1 mg P/kg corresponds to 16.13 μmol/kg). In the case of the given dosages, it is always a question of the daily dosage.

In the case of the evaluation, the retinoid-induced increase of the calcium level (difference of day 3 to day 0) is taken as 100%. The action of a biphosphonate (% rel. inhibition) was defined as the inhibition of the retinoid-induced calcium increase by this biphosphonate in comparison with the retinoid effect. If the calcium level with biphosphonate administration increased by the same value after retinoid administration alone, then the action of the biphosphonate was 0%; if no increase of the calcium level took place, then the action was 100%; if the calcium level dropped below the initial value, then the action was greater then 100%.

The calculation of the action (% rel. inhibition) in this assay took place according to the following formula:

$$\% \text{ rel. inhibition} = \frac{\text{delta } Ca_R - \text{delta } Ca_{BP}}{\text{delta } Ca_R} \times 100$$

delta $Ca_R$: difference of the serium calcaemia which was induced after retinoid administration (on three successive days) and their basal value delta $Ca_{BP}$: difference of the serium calcaemia which (was induced) after retinoid administration (on three successive days) with corresponding biphosphonate administration and their basal value,

TABLE

| compound | dose mg P/kg | administration | % rel. inhibition | n |
|---|---|---|---|---|
| Example 1 | 0.010 | s.c. | 57.07 | 5 |
|  | 0.030 | s.c. | 103.92 | 5 |
| pamidronate | 0.010 | s.c. | 29.12 | 5 |
|  | 0.030 | s.c. | 37.52 | 5 | pamidronate = 1-hydroxy-3-aminopropyl-1,1-diphosphonic acid

We claim:

1. A compound of the formula

wherein R$^1$ is hydrogen, a straight-chained or branched, saturated or unsaturated C$_{1-9}$ alkyl radical which is unsubstituted or substituted by phenyl which in turn is unsubstituted or substituted by C$_{1-3}$ alkyl, C$_{1-3}$ alkoxy or halogen;

each R$^2$, which may be the same or different, is hydrogen or C$_{1-3}$ alkyl;

R is hydrogen or a straight-chained or branched C$_{1-4}$ alkyl radical;

X is a C$_{1-6}$ alkylene chain which is unsubstituted or substituted at least once by C$_{1-3}$ alkyl, or by 1 or 2 carbon atoms of the alkylene chain being ring atoms of a cyclopentyl or cyclohexyl ring, said alkylene chain being uninterrupted or interrupted by an oxygen atom; and Y is hydroxyl;

or a pharmacologically acceptable salt thereof.

2. Compound of claim 1, wherein X is ethylene, propylene, butylene, 1-methylpropylene, 2-methylpropylene, 1-methylbutylene or 2-methylbutylene.

3. Compound of claim 1, wherein X is a 1,1- or 1,2-substituted cyclohexyl or cyclopentyl ring connected to the bisphosphonic acid moiety by a methylene, ethylene or propylene bridge.

4. Compound of claim 1, wherein R is hydrogen, methyl, ethyl or isobutyl.

5. Compound of claim 1, wherein R and R$^2$ are each hydrogen and R$^1$ is hydrogen or alkyl.

6. Compound of claim 1, wherein X is methylene, ethylene, propylene or butylene.

7. Compound of claim 1, wherein the compound is 1-hydroxy-3-iminoethyl-aminopropane-1,1-disphosphonic acid.

8. Compound of claim 1, wherein the compound is selected from the group consisting of 1) 1-hydroxy-2-(1-iminoethyl)-aminoethane-1,1-diphosphonic acid 2) 1-hydroxy-4-(1- iminoethyl)-aminobutane-1,1-diphosphonic said 3) 1-hydroxy-5-(1-iminoethyl)-aminopentane-1,1-diphosphonic acid 4) 1-hydroxy-3-(1-iminopropyl)-aminopropane-1,1diphosphonic acid 5) 1-hydroxy-4-(1-iminobutyl)-aminobutane-1,1-diphosphonic acid 6) 1-hydroxy-6-(1-iminoethyl)-aminohexane-1,1-diphosphonic acid
7) 1-hydroxy-3-(1-iminoethyl)-aminobutane-1,1-diphosphonic acid
8) 1-hydroxy-4-(iminoethyl)-aminopentane-1,1-diphosphonic acid
9) 1-hydroxy-5-(1-iminoethyl)-aminohexane-1,1,-diphosphonic acid
10) 1-hydroxy-3-(1-iminopropyl)-aminobutane-1,1-diphosphonic acid
11) 1-hydroxy-4-(iminoethyl)-amino-3-methylbutane-1,1-diphosphonic acid
12) 1-hydroxy-3-(1-iminobutyl)-aminopropane-1,1-diphosphonic acid
13) 1-hydroxy-3-[1-(methylimino )-ethyl]-aminopropane-1,1-diphosphonic acid
14) 1-hydroxy-3-[2-(1-iminoethyl)-aminocyclohexyl]-propane-1,1-diphosphonic acid
15) 1-hydroxy-3-[2-(1-iminoethyl )-aminocyclopentyl]-propane-1,1-diphosphonic acid
16) 1-hydroxy-3-[1-(1-iminoethyl)-aminocyclohexyl]-propane-1,1-diphosphonic acid
17) 1-hydroxy -2-[2-(1-iminopropyl)-aminocyclohexyl]-ethane-1,1-diphosphonic acid
18) 1-hydroxy-2-(iminomethyl)-aminoethane-1,1-diphosphonic acid
19) 1-hydroxy-3-(iminomethyl)-aminopropane-1,1-diphosphonic acid, and
20) 1-hydroxy-3-[2-(iminomethyl)-aminocyclohexyl]-propane-1,1-diphosphonic acid.

9. Pharmaceutical composition suitable for the treatment of calcium metabolism disturbances comprising a compound of claim 1 and a pharmaceutically acceptable carrier therefor.

10. A method of treating a calcium metabolism disturbance in a patient in need of such treatment comprising administering a calcium metabolism disturbance treating effective amount of a compound of claim 1 to said patient.

11. Method of claim 5, wherein the disturbance is osteoporosis, Paget's disease or Bechterew's disease.

12. A process for producing a compound of claim 1 comprising reacting a carboxylic acid of the formula

wherein $R^1$, $R^2$ and X are defined in claim 5, with a mixture of (a) at least one of phosphorous acid and phosphoric acid and (b) at least one of a phosphorus halide and a phosphoryl halide.

* * * * *